US006214354B1

United States Patent
Calandra et al.

(10) Patent No.: US 6,214,354 B1
(45) Date of Patent: *Apr. 10, 2001

(54) METHOD FOR PREVENTING ZOSTER OR ALLEVIATING VARICELLA RELATED POST-HERPETIC NEURALGIA

(75) Inventors: Gary B. Calandra, Blue Bell; Philip J. Provost, Lansdale, both of PA (US); Myron J. Levin, Denver, CO (US); C. Jo White, Gwynedd, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/372,535

(22) Filed: Aug. 11, 1999

Related U.S. Application Data

(63) Continuation of application No. 08/419,223, filed on Mar. 18, 1994, now Pat. No. 5,997,880, which is a continuation of application No. 07/915,141, filed on Jul. 17, 1992, now abandoned.

(51) Int. Cl.$^7$ ................................................... A61K 39/245
(52) U.S. Cl. .................................. 424/230.1; 424/196.11; 424/202.1; 424/204.1; 424/229.1; 435/5; 435/7.1; 435/173.3
(58) Field of Search .................... 424/229.1, 230.1, 424/196.11, 202.1, 204.1; 435/5, 7.1, 173.3

(56) References Cited

U.S. PATENT DOCUMENTS

| | | | |
|---|---|---|---|
| 3,985,615 | 10/1976 | Kabo | 195/1.3 |
| 4,000,256 | 12/1976 | Hilleman et al. | 424/89 |
| 4,008,317 | 2/1977 | Gits | 424/89 |
| 4,147,772 | 4/1979 | McAleer et al. | 424/89 |
| 4,191,745 | 3/1980 | Mayr et al. | 424/90 |
| 4,273,762 | 6/1981 | McAleer et al. | 424/89 |
| 4,337,242 | 6/1982 | Markus et al. | 424/89 |
| 4,338,335 | 7/1982 | McAleer et al. | 424/361 |
| 4,686,101 | 8/1987 | Ellis et al. | 424/88 |
| 4,769,239 | 9/1988 | Ellis et al. | 424/89 |
| 4,812,559 | 3/1989 | Ellis et al. | 536/27 |
| 4,952,674 | 8/1990 | Keller et al. | 530/326 |
| 5,024,836 | 6/1991 | McAleer et al. | 424/89 |

FOREIGN PATENT DOCUMENTS

| | | |
|---|---|---|
| 0 101 200 A2 | 7/1983 | (EP) . |
| 0 211 756 A1 | 7/1986 | (EP) . |
| 0 251 534 A1 | 6/1987 | (EP) . |
| 0 405 867 A1 | 6/1990 | (EP) . |
| WO 92/06989 | 4/1992 | (WO) . |

OTHER PUBLICATIONS

Bennett, et al., "The Effects of Freeze-Drying on the Potency and Stability of Live Varicella Virus Vaccine", Dev. Biol. Stand., vol. 74, pp. 215–221, (Kargel, Basel, 1991).

Provost, et al., "Antibody assays suitable for assessing immune responses to live varicella vaccine", Vaccine, vol. 9, Feb. 1991, pp. 111–116.

Hardy, et al., "The Incidence of Zoster After Immunization with Live Attenuated Varicella Vaccine", New England J. of Med., vol. 325, No. 22, pp. 1545–1550, Nov. 28, 1991.

Hayward, et al., "Varicella-Zoster Virus (VZV)-Specific Cytotoxicity after Immunization of Nonimmune . . . ", J. of Infect. Dis., vol. 166, pp. 260–264, Aug. 1992.

Sperber, et al., "Serologic response and reactogenicity to booster immunization of healthy seropositive . . . ", Antiviral Research, vol. 17, pp. 213–222 (1992).

Keller, et al., "Three Major Glycoprotein Genes of Varicella-Zoster Virus Whose Products Have . . . ", J. of Virol., vol. 52, No. 1, Oct. 1984, pp. 293–297.

Keller, et al., "Purification of individual varicella-zoster virus (VZV) glycoproetins gpI, gpII, and gpIII . . . ", J. of Virol. Methods, vol. 14 (1986), pp. 177–188.

Davison, et al., "New Common Nomenclature for Glycoprotein Genes of Varicella-Zoster Virus and Their . . . ", J. of Virol., vol. 57, No. 3, Mar. 1986, pp. 1195–1197.

Neff, et al., "Clinical and Laboratory Studies of KMcC Strain Live . . . ", Proceedings of the Society for Experimental Biology and Medicine, vol. 166, pp. 339–347 (1981).

Mayo, et al., "Varicella Zoster-Associated Neurologic Disease Without Skin Lesions", Arch. Neurol., vol. 46, Mar. 1989, pp. 313–316.

Gnann, et al., "Natural history and treatment of varicella-zoster in high-risk populations", J. of Hospital Infection, 1991, vol. 18, (Suppl. A), pp. 317–329.

Croen, "Varicella-Zoster Virus Latency", Annu. Rev. Microbiol., 1991, vol. 45, pp. 265–282.

Junker, et al., "Recurrent varicella-zoster virus infections in apparently immunocompetent children", Pediatr. Infect. Dis. J., 1991, vol. 10, pp. 569–577.

Christiansen, et al., "Early herpes zoster infection in adult patients with Hodgkins's disease undergoing . . . ", Bone Marrow Transplantation, 1991, vol. 7, pp. 435–437.

Vafai, et al., "Detection of Antibodies to Varicella-Zoster Virus Proteins in Sera from the Elderly", Gerontology, 1988, vol. 34, pp. 242–249.

Ragozzino, et al., "Risk of Cancer After Herpes Zoster", The New England J. of Med., vol. 307, No. 7, pp. 393–397, Aug. 12, 1982.

Wilson, et al., "Subclinical Varicella-Zoster Vuris Viremia, Herpes, Zoster, and T Lymphocyte Immunity . . . ", J. of Infect. Dis., 1992, vol. 165, pp. 119–126.

(List continued on next page.)

Primary Examiner—Jeffrey Stucker
Assistant Examiner—Ulrike Winkler
(74) Attorney, Agent, or Firm—Joseph A. Coppola; Jack L. Tribble

(57) ABSTRACT

Herpes Zoster, or varicella related post herpetic neuralgia is alleviated by immunizing people at risk of developing herpes zoster with varicella zoster virus (VZV) antigen.

4 Claims, No Drawings

OTHER PUBLICATIONS

Lawrence, et al., "The Risk of Zoster After Varicella Vaccination in Children With Leukemia", New England J of Med, vol. 318, pp. 543–548 (1992).
Hardy, et al., "Zoster After Live Attenuated Varicella Vaccine", Abstracts of the 1990 ICAAC, No. 723.
Levin, et al., "Use of Live, Attenuated Varicella–Zoster virus (VZV) Vaccine to Boost the VZV Immune . . . ", Abstracts of the 1990 ICAAC, No. 724.
Plotkin, et al., "Zoster in Normal Children After Varicella Vaccine", The Journal of Infectious Disease , vol. 159, No. 5, May 1989, pp. 1000–1001.
Brunell, et al., "Risk of Herpes Zoster in Children With Leukemia: Varicella Vaccine Compared With History . . . ", Pediatrics, vol. 77, No. 1, pp. 53–56. (No year).
Antonelli, et al., Herpes Zoster in Patients with Rheumatoid Arthritis Treated with Weekly, Low–Dose . . ., The American Journal of Medicine, vol. 90, Mar. 1991, pp. 295–298.
Schmader, et al., "Are Stressful Life Events Risk Factors for Herpes Zoster?", Amer. Geriatrics Soc., vol. 38, pp. 1188–1194, (1990).
Williams, et al., "Herpes zoster following varicella vaccine in a child with acute lymphocutic leukemia", J. of Pediatr., vol. 106, pp. 259–261, 1985.
Ljungman, et al., "A randomized trial of oral versus intravenous acyclovir for treatment of herpes zoster . . . ", Bone Marrow Transplantation (1989), vol. 4, pp. 613–615.
Hammerschiag, et al. "Hespes Zoster in an Adult Recipient of Live Attenuated Varicella Vaccine", J. of Infect. Dis., vol. 160, No. 3, Sep. 1989, pp. 535–537.
Frank, et al., "Multiple Ischemic Infarcts in a Child with AIDS, Varicella Zoster Infection, and Cerebral Vasculitis", Pediatric Neurol., vol. 5, pp. 64–67, 1988.
Gershon, et al., "Antibody to Varicella–Zoster Virus in Parturient Woman and Their Offspring During . . . ", Pediatrics, vol. 58, No. 5, Nov. 5, 1976, pp. 592–696.
Lipton, et al., Management of Varicella Exposure in a Neonatal Intensive Care Unit, JAMA, Mar. 24–31, 1989, vol. 261, No. 12, pp. 1782–1784.
Duby, et al., "Sequestraton of virus–specific T cells in the cerebrospinal fluid of a patient with varicella zoster . . . ", J. of Neuroimmunology, vol. 22, (1989), pp. 63–68.
Leventon–Kriss, et al., "Seroepidemiologic Aspects of Varicella Zoster Virus Infections . . . ", J. Med. Sci., vol. 14, No. 7, Jul. 7, 1978, pp. 766–770.
Reboul, et al., "Herpes Zoster and Varicella Infections in Children with Hodgkin's Disease", Cancer, Jan. 1978, vol. 41, pp. 95–99.
Rusthoven, et al., "Varicella–Zoster Infection in Adult Cancer Patients", Arch. Intern. Med., vol. 148, Jul. 1988, pp. 1561–1566.
Bolin, et al., "Airborne Transmission of Nosocomial Varicella from Lacalized Zoster", J. of Infectious Diseases, vol. 158, No. 1, Jul. 1988, pp. 238–247.
Croen, et al., "Patterns of gene expression and sites of latency in human nerve ganglia are different . . . ", Proc. Natl. Acad. Sci. USA, vol. 85, pp. 9773–9777. (No year).
Webster, et al., "Titration of IgG Antibodies Against Varicella Zoster Virus Before Bone Marrow Transplantation . . . ", J. of Med. Virol., vol. 27, pp. 117–119 (1989).
"Varicella vaccine seen to help prevent herpes in the elderly", Infectious Disease News, vol. 2, No. 3, Mar. 1999.

Kobayashi, et al. "Varicella–Zoster Virus Infection in Chronis Granulomatous Disease", The Pediatr. Infect. Dis. J., vol. 7, No. 11, Nov. 1988, pp. 809–810.
Berger, et al., "Restoration of Varicella–Zoster Virus Cell–Mediated Immune Response After Varicella . . . ", Postgraduate Medical Journal, 1985, vol. 61, Suppl. 4, pp. 143–145.
Hayward, et al., "Varicella–Zoster Virus–Specific Immunity After Herpes Zoster", J. of Infect. Dis., 1991, vol. 163, pp. 873–875.
Wei–Hai, et al. "Experimental Studies on the Prevention and Treatment of Chickenpox and Herpes . . . ", Chinese Medical Journal, vol. 102, No. 5, pp. 395–399, 1989.
Peterslund, "Management of Varicella Zoster Infections in Immunocompetent Hosts," The American Journal of Medicine, vol. 85, Suppl. 2A, Aug. 29, 1988, pp. 74–78.
Balfour, et al., "Varicella Zoster Virus Infections in Immunocompromised Hosts", The American Journal of Medicine, vol. 85, Suppl. 2A, Aug. 29, 1988, pp. 68–78.
Arvin, et al., "Immunologic Evidence of Reinfection with Varicella–Zoster Virus", J. of Infect. Dis., vol. 148, No. 2, Aug. 1983, pp. 200–205.
Luby, et al., "A Longitudinal Study of Varicella–Zoster Virus Infections in Renal Transplant Recipients", J. of Infect. Dis., vol. 135, No. 4, Apr. 1977, pp. 659–663.
Harper, et al., "IgM and IgG Responses to Varicella–Zoster Virus p32/p36 Complex After Chickenpox and Zoster . . . ", J. of Infect. Dis., vol. 153, No. 3, Mar. 1989, pp. 444–451.
Vafai, et al., "Expression of varicella–zoster virus in blood mononuclear cells of patients with postherpetic neuralgia", Proc. Natl. Acad. Sci. USA, vol. 85, pp. 2767–2770, Apr. 1988.
Ragozzino, et al., "Population–Based Study of Herpes Zoster and Its Sequelae", Medicine, vol. 61, pp. 310–316 (1982).
Guess, et al., "Epidemiology of Herpes Zoster in Children and Adolescents: A Popuulation–Based Study", Pediatrics, vol. 76, No. 4, Oct. 1985.
Hilleman, et al., "New Developments with New Vaccines", New Developments With Human and Veterinary Vaccines, pp. 21–49, 1980.
Guess, et al., "Chichenpox Hospitalizations Among Residents of Olmstead County, Minnesota, 1962Through 1981", AJDC, vol. 138, pp. 1055–1057 (1984).
Asano, et al., "Immonogenicity of Wild and Attenuated Varicella–Zoster Virus Strains in Rhesus Monkeys", J. of Med. Virol., vol. 14, pp. 305–313. (No year).
Weibel, et al., "Live Attenuated Varicella Virus Vaccine", The New England Journal of Medicine, vol. 310, pp. 1409–1415, May 31, 1984.
Hilleman, et al., "Whither Immunization Against Viral Infections", Annals of Internal Medicine, 1984, vol. 101, pp. 852–858.
Ellis, et al., Use of a Bacterial Expression Vector to Map the Varicella–Zoster Virus Major Glycoprotein Gene . . . , J. of Virol., Jan. 1985, pp. 81–88.
Weibel, et al., "Livr Oka/Merck Varicella Vaccine in Healthy Children", JAMA, vol. 254, (1985), pp. 2435–2439.
Guess, et al., "Population–Based Studies of Varicella Complications", Pediatrics, 1986, pp. 723–727.
Keller, et al., "Identification and Structure of the Gene Encoding gpII, a Major Glycoprotein of Varicella–Zoster Virus", Virology, vol. 152, pp. 181–191 (1986).

Lowe, et al., "Expression of Epstein–Barr Virus Major Envelope Glycoprotein gp250/220 by a Recombinant . . . ", Vaccines, vol. 87, pp. 364–367 (1987).

Keller, et al., "Identification and Sequence of the Gene Encoding gpIII, a Major Glycoprotein of Varicella–Zoster Virus", Virology, vol. 157, pp. 526–533 (1987).

Emini, et al., "Identification of an Epstein–Barr Virus Glycoprotein Which Is Antigenically Homologous . . . ", Virology, vol. 157, pp. 552–555 (1987).

Lowe, et al., "Varicella–zoster virus as a live vector for the expression of foreign genes", Proc. Natl. Acad. Sci. USA, vol. 84, pp. 3896–3900, Jun. 1987.

Brunell, et al., "Antibodies to the Three Major Glycoproteins of Varicella–Zoster Virus: Search for . . . ", J. of Infect. Dis., vol. 156, No. 3, Sep. 1987, pp. 430–435.

Provost, et al., "Successful Infectio of the Common Marmoset (Callithrix jacchus) with Human Varicella . . . ", J. of Virology, vol. 61, pp. 2951–2955. (No year).

Solke, et al., "Immunization of Monkeys with Varicella–Zoster Virus Glycoprotein Antigens and Their Response . . . ", J. of Med. Virol., vol. 22, pp. 307–313, 1987.

Ellis, et al., "Varicella–Zoster Vaccine", Vaccines and Immunotherapy, pp. 326–336. (No year).

Watson, et al., "Cell–Mediated Immune Responses after Immunization of Healthy Seronegative Children . . . ", J. of Infect. Dis., vol. 160, 1990, pp. 794–799.

Krah, et al., "Enhancement of varicella–zoster virus plaquing efficiency with an agarose overlay medium", J. of Virol. Methods, vol. 27, 1990, pp. 319–326.

Wasmuth, et al., "Sensitive Enzyme–Linked Immunosorbent Assay for Antibody to Varicella–Zoster . . . ", J. of Med. Virol., vol. 32, pp. 189–193 (1990).

Kuter, et al., Oka/Merck varicella vaccine in healthy children: final report of a 2–year efficacy study . . . , Vaccine, vol. 9, Sep. 1991, pp. 643–647.

White, et al., "Varicella Vaccine (Varivax) in Healthy Children and Adolescents: Results From Clinical Trials . . . ", Pediatrics, vol. 87, No. 5, May 1991, pp. 604–610.

Ellis, et al., "Immunogenicity in the Common Marmoset of a Recombinant Varicella–Zoster Expressing Epstein–Barr . . . ", Technological Advances in Vaccine Develop., pp. 235–241. (No year).

Lydick, et al., "Association of steroid therapy with vaccine–associated rashes in children with acute lymphocytic . . . ", Vaccine, vol. 7, Dec. 1989, pp. 549–553.

Straus, et al., "Varicella–Zoster Virus Infections", Annals of Internal Medicine, vol. 108, 1988, pp. 221–237.

Hyman, et al., "Varicella–Zoster Virus RNA in Human Trigeminal Ganglia", The Lancet, Oct. 8, 1983, pp. 814–816.

Gilden, et al., "Varicella–zoster virus DNA in human sensory ganglia", Nature, vol. 306, 1983), pp. 478–480.

Mahalingam, et al., "Latent Varicella–Zoster Viral DNA in Human Trigeminal and Thoraci Ganglia", vol. 323, 1990, pp. 627–631.

Hope–Simpson, et al., "The Nature of Herpes Zoster: A Long–Term Study and a New Hypothesis", Proc. of the Royal Soc. of M ed., vol. 52, (1957), pp. 9–12.

Moragas, et al., "The Outcome of Patients with Herpes Zoster", A.M.A. Arch. of Derm., vol. 75, 1957, pp. 193–196.

Watson, et al., "Postherpetic Neuralgia", Neurologic Clinics, vol. 7, 1989, pp. 231–247.

Rowbotham, et al., "Post–herpetic neuralgia: the relation of pain complaint, sensory disturbance . . . ", Pain, vol. 39, 1989, pp. 129–144.

Miller, et al., "Selective decline in cellular immune response to varicella–zoster in the elderly", Neurology, vol. 30, 1980, pp. 582–587.

Burke, et al., "Immune Responses to Varicella–Zoster in the Aged", Arch. Intern. Med., vol. 142, 1987, pp. 291–293.

Hayward, et al., "Lymphocyte Responses to Varicella Zoster Virus in the Elderly", J. of Clinical Immunol., vol. 7, No. 2, pp. 174–178. (No year).

Feldman, et al., "Herpes Zoster in Children With Cancer", Am. J. Dis. Child., vol. 126, Aug. 1973, pp. 178–184.

Dolin, et al., "Herpes–Zoster Varicella Infections in Immunosuppressed Patients", Annals of Internal Medicine, vol. 89, 1978, pp. 375–388.

Melbye, et al., "Risk of Aids After Herpes Zoster", The Lancet, Mar. 28, 1987, pp. 728–730. (No year).

Asano, et al., Long–Term Protective Immunity of Recipients of the OKA Strain of Live Varicella Vaccine, Pediatrics, vol. 75, No. 4, Apr. 1985, pp. 667–671.

Arbeter, et al., "Varicella Vaccine Studies in Healthy Children and Adults", Vaccine in Healthy Animals, 1986, pp. 748–756.

Gershon, et al., "Immunization of Healthy Adults with Live Attenuated Varicella Vaccine", J. of Infect. Dis., vol. 158, No. 1, Jul. 19 88, pp. 132–137. (No year).

Berger, et al., "Enhancement of Varicella–Zoster–Specific Immune Responses in the Elderly by Boosting . . . ", J. of Infect Dis., vol. 149, No. 4, Apr. 1984, p. 647.

Berger, et al., "Booster Vaccination of Healthy Adults With VZV Antibody But Without A VZV–Specific Cell–Mediated . . . ", Antiviral Res. Suppl. 1 (1985), pp. 267–271.

Henry, et al., Limiting Dilution Analysis, In Vitro Imm. Resp., pp. 138–152. (No year).

Laird, et al., "Random–Effects Models for Longitudinal Data", Biometrics, vol. 38, pp. 963–974, Dec. 1982.

Jennrich, et al., "Unbalanced Repeated–Measures Models with Structured Covariance Matrices", Biometrics, vol. 42, pp. 805–820, Dec. 1986.

Nelder, "Inverse Polynomials, A Useful Group of Multi–Factor Response Functions", Biometrics, (1966), pp. 128–141.

Beverley, "Human T–Cell Memory", Current Topics in Microbiol. & Imm., vol. 159, 1990, pp. 111–122.

Hayward, et al., "Phenotype, Cytotoxic, and Helper Functions of T Cells from Varicella Zoster Virus . . . ", Viral Immunology, vol. 2, 1989, pp. 175–184.

Gershon, et al., "Antibody Responses to Varicella–Zoster Virus and the Role of Antibody in Hose Defense", Am. J. of the Med. Sci., vol. 282, 1986, pp. 12–17.

Hayward, et al., "Herpes Simplex Virus–Stimulated γ–Interferon Production by Newbord Mononuclear Cells", Pediatric Research, vol. 20, 1986, pp. 398–401.

Leibson, et al., "Inhibition of Herpes Simplex Virus Type 1 Replication in Fibroblast Cultures by Human . . . ", J. of Virology, vol. 57, No. 3, Mar. 1986, pp. 976–982.

Goodwin, et al., "Immunological responses of a healthy elderly population", Clin. Exp. Imm., vol. 48, 1982, pp. 403–410.

Tice, et al., "Cytokinetic Analysis of the Impaired Proliferative Response of Peripheral Lymphocytes . . . ", vol. 00, 1979, p;p. 1029–1041.

Murasko, et al., "Immunologic Response in an Elderly Population with a Mean Age of 85", The American Journal of Medicine, vol. 81, 1986, pp. 612–618.

Nagel, et al., "Enumeration of T Lymphocyte Subsets by Monoclonal Antibodies in Young and Aged Humans", J. of Immunol., vol. 127, 1981, pp. 2086–2088.

Thompson, et al., "The Immune Status of Healthy Centenarians", J. of Amer. Ger., vol. 32, 1984, pp. 274–281.

Staiano–Coico, et al., "Immunologicl Studies of Aging", J. of Immunol., vol. 132, 1984, pp. 1788–1792.

Sohnle, et al., "Age–related effects on the number of human lymphocytes in culture initially responding . . . ", Clin. Exp. Imm., vol. 47, 1982, pp. 138–146.

Dutkowski, et al., "Increases chromosomal instability in lymphocytes from elderly humans", Mutation Research, vol. 149, 1985, pp. 505–512.

Chopra, et al., "Interleukin 2, Interleukin 2 Receptor, and Interferon–$\gamma$ Synthesis . . . ", Clinical Immunol. and Immunopathy, Clin. Imm. & Immunopath., vol. 53, 1989, pp. 297–308.

Arbeter, et al., "Varicella vaccine studies in healthy children an adults", Pediatrics, vol. 78 (4 Pt. 2), Oct. 1986, pp. 745–756.

Yabuuchi, et al., "A Live Varicella Vaccine in a Pediatric Community", Biken Journal, vol. 27, 1984, pp. 43–49.

Tortora, et al., "T Cells and Cell–Mediated Immunity", Microbiology: An Introduction, pp. 424–426. Pub. 1989.

Lazar, et al., "Transforming Growth Factor $\alpha$: Mutation of Aspartic Acid 47 and Leucine 48 Results . . . ", Mol. and Cell. Biol., vol. 8, No. 3, 1988, pp. 1247–1252.

SmithKline Beecham, Live Attenuated Varicella Vaccine. (No year).

Varis, et al., "Efficacy of High–Titer Live Attenuated Varicella Vaccine in Healthy Young Children", J. Infect. Dis., vol. 174, (Suppl. 3), 1996, pp. S330–S334.

METHOD FOR PREVENTING ZOSTER OR ALLEVIATING VARICELLA RELATED POST-HERPETIC NEURALGIA

This application is a continuation of U.S. patent application Ser. No. 08/419,223, filed Mar. 18, 1994, now U.S. Pat. No. 5,997,880, which is a continuation of U.S. patent application Ser. No. 07/915,141, filed Jul. 17, 1992, now abandoned, the disclosures of which are hereby incorporated by reference in their entireties.

BACKGROUND OF THE INVENTION

Post-herpetic neuralgia is the predominant morbidity associated with development of herpes-zoster, also known as shingles. The neuralgia typically lasts for from one to six months and is often excruciatingly painful.

Evidence has accrued in recent years which shows that herpes-zoster is caused by reactivation of latent varicella virus [Straus et al., *Ann. Int. Med.* (1988); 108, 221–237; Hyman et al., *Lancet* (1983) 2, 814–816; Gilden et al., *Nature* (1983) 306, 478–80; Croen et al., *Proc. Natl. Acad. Sci. USA* (1988); 85, 9773–9777; Mahalingham at al., *New Eng. J. Med.* (1990) 323, 627–631]. The initial varicella infection may have occurred as a result of infantile chickenpox or as a result of immunization with a live-attenuated varicella zoster virus vaccine to prevent chickenpox. In either case, the virus appears to remain in the infected individual's system long after chickenpox or vaccination. The locus of VZV latency appears to be neural cells within dorsal root ganglia.

Years after VZV has become latent, the virus reactivates by an as yet poorly understood mechanism. Nonetheless, the reactivation of VZV and its subsequent replication gives rise to herpes zoster. It is in the course of and subsequent to this reactivation of VZV that severe post-herpetic neuralgia develops.

Numerous reports in the literature have suggested that there may be a correlation between diminished immune competence and reactivation of herpes zoster from its latent state. Suggestions of the mechanism by which reactivation occurs include diminished cell-based immunity, such as reduction of the number of blood $CD4^+$ receptor bearing T-lymphocytes, which are responsible for recognizing non-self antigens presented by MHC type II molecules following phagocytosis of VZV. Alternatively, the reduced levels of $CD8^+$ T-lymphocytes, responsible for killing cells in which MHC type I molecules recognize and present non-self antigens, has also been suggested as a possible mechanism perimissive for VZV reactivation. Neumeyer et al., [*N.E.J. Med.* p. 1456, May 29, 1986) noted a drop in the ratio of $CD4^+/CD8^+$ prior to zoster, and subsequent increase of the ratio upon termination of the clinical syndrome.

In one study, a varicella vaccine was adminsitered to elderly subjects in an attempt to boost their CMI responses to VZV. VZV immunization of these seropositive individuals was undertaken because of the previously described age-related decline in VZV-specific CMI [Miller A E., *Neurology.* (1980); 30, 582–587; Berger R, Florent G. Just M., *Infect. Immun.* (1981); 32, 24–27; Burke B L, Steele, R W, Beard O W., *Arch. Intern. Med.* (1982); 142, 291–293] and the possibility that the age-related reactivation of VZV (as herpes zoster) is a consequence of this decline. This live attenuated vaccine was well tolerated; no severe local or systemic reactions occurred and the mild reactions were not very common. Systemic spread of vaccine virus, as manifested by minimal skin rash, did occasionally occur (possibly in 6/245 injections). While this is of theoretical concern in elderly patients with documented reduction of specific cell-mediated immunity, the resulting lesions and symptoms proved to be of no clinical significance. This is consistent with anecdotal observations that seropositive grandparents are not infected after exposure to grandchildren with varicella.

The deficits in VZV-specific immunity in the elderly occur in the context of generally reduced CMI responses. These are detected in assays of delayed hypersensitivity skin responses [Goodwin J S, et al., *Clin. Exp. Immunol.* (1982); 48, 403–410] and in in vitro proliferative responses of T lymphocytes stimulated by mitogens [Hayward A R, et al., *J. Clin. Immunol.* (1987); 7, 174–178; Tice R R, et al., *J. Exp. Med.* (1979); 149, 1029–1041; Murasko D M, et al., *Am. J. Med.* (1986); 81, 612–618]. Most studies document normal T cell number, but there is a decrease in $CD4^+$ cells [Nagel Je, et al., *J. Immunol.* (1981); 127, 2086–2088; Thompson J S, at al., *J. Am. Geriate Soc.* (1984); 32, 274–281]. Natural killer cell number and function are normal in these patients [Hayward A R, Herberger M., *J. Clin. Immunol.* (1987); 7, 174–178; Nagel Je, et al., *J. Immunol.* (1981); 127, 2086–2088]. An increased cell cycle time, as suggested in the study of Tice et al, would be a possible explanation for the loss of CMI with aging [Tice R R, et al., *J. Exp. Med.* (1979); 149, 1029–1041]. However, subsequent studies do not favor a change in cell cycle or any reduction in the degree of clonal expansion following antigen stimulation [Staiano-Coico L, et al., *J. Immunol.* (1984); 132, 1788–1792; Sohnie P G, et al., *Clin. Exp. Immunol.* (1982); 47, 138–146]. Instead, DNA analyses show an increased frequency of DNA damage, sister chromatid exchanges, and cell loss in mitogen stimulated cells from the elderly [Dutkowski R T, et al., *Mutat. Res.* (1985); 149, 505–512]. Reduced proliferative responses to mitogens are not necessarily accompanied by reduced IL2 or IL2R synthesis [Dutkowski R T, et al., *Mutat. Res.* (1985); 149, 505–512]. The most consistent defect found by Chopra et al., was increased gamma-interferon production and a reduced survival of stimulated cells which supports the use of a booster [Chopra R K, et al., *Clin. Immunol. Immunopathol.* (1989); 53, 297–308].

Other studies in an aging population showed that the reduced VZV-specific immunity which accompanies the increased incidence of HZ in the elderly is at least partially explained by a reduced frequency of VZV-specific $CD4^+$ cells in blood. However, these patients have normal T cell numbers and their NK cell activity is preserved in response to VZV antigen, providing that sufficient IL2 is present [Hayward A R, et al., *J. Clin. Immunol.* (1987); 7, 174–178]. The frequency of T cells expressing the memory cell phenotype (CD45RO) increases with age from a mean of 43+17% at 28 years to 65+14% at 70 years, so the decline in VZV-specific immunity with aging is not due to a selective loss of this subset. $CD45RO^+$ cells make more γ-interferon than $CD45RA^-$ cells, correlating with the results of Chopra and co-worker.

Whatever the mechanism of zoster control or reactivation, no medical evidence has effectively demonstrated prevention of herpes zoster reactivation (zoster), or diminution of post-herpetic neuralgia. Chemotherapeutic agents as a class have been dismal in adressing this painful condition [Watson, C. P. N., *Neurol. Clin.,* 7, 231–248 (1989); Straus, et al., *Ann. Int. Med.* 108, 221–237 (1988)].

This invention is a method for reducing post-herpetic neuralgia and for ameliorating or abrogating herpes zoster reactivation. The efficacy of the method is demonstrated by positive results obtained in vivo in which the level of VZV specific lymphocytes increases. This increase in responder cell frequency, RCF, induced by immunization according to the method of this invention, yields an immune state in vivo which is refractory to the diseased state, including VZV reactivation and post herpetic neuralgia. Broad based, multicenter, long-term clinical investigation in which at-risk individuals are administered live-attenuated, killed, or subunit antigens, purified from VZV or from recombinant production shows that immunization according to this invention results in significant protection against VZV reactivation, or if reactivation occurs, significant reduction in the duration or severity of the post herpetic neuralgia.

SUMMARY OF THE INVENTION

A method is described for alleviating post-herpetic neuralgia and for ameliorating or abrogating herpes zoster reactivation in at-risk people, which utilizes VZV antigenic stimulation. The VZV antigen is a live-attenuated VZV virus, a killed-whole VZV virus, or a purified VZV subunit antigen from whole VZV or from recombinant expression.

At-risk individuals are those having had varicella (chickenpox), even if subclinically, or having had a live varicella vaccine. Particularly at-risk are elderly or immunocompromised individuals. At-risk status may be confirmed by positive serum anti-VZV antibodies or positive response to a VZV antigen skin test. Particularly indicative of at-risk status is a VZV responder cell frequency below about 1 responder cell in 68,000 while a protected state is approached when the RCF is closer to 1 responder cell in 40,000.

At-risk individuals are administered the VZV antigen in an immunologically effective amount and monitored for return to at risk status, at which point another immuniztion may be undertaken.

The efficacy of the method is demonstrated by positive results obtained in a broad based, multicenter, long-term clinical investigation.

DETAILED DESCRIPTION OF THE INVENTION

In the method of this invention, an individual at-risk of developing herpes-zoster is immunized with a VZV antigen to induce elevation of anti-VZV immune responses. This immunization reduces the severity of post-herpetic neuralgia associated with VZV reactivation, and it reduces or prevents the reactivation event itself. In particular embodiments, at least 1,000 plaque forming units (PFU) of live varicella vaccine is used. In other embodiments, the severity of post-herpetic neuralgia is reduced to a period of less than one month following the development of zoster.

An at-risk individual includes anyone that has experienced chickenpox, even of subclinical severity, and anyone that has received a live varicella zoster virus vaccination. Those among this class who are particularly at-risk are people who, for one reason or another, are immunocompromised. This may be due to development of an acquired immune deficiency disease (e.g., AIDS, ARC) or due to chemotherapy or other immunosuppressive therapy (e.g., graft rejection immunosuppression). In addition, the incidence of zoster increases with age. Among at-risk people over 50, incidence is 2.5–5.0 cases/1,000 people/year. By age 80, the incidence rises to 5–10 cases/1,000 people/year. This increased risk correlates with declining cell-mediated immunity to VZV.

To establish that someone is an at-risk individual, without reliance on personal records or recollection, a simple skin-test may be performed as described in the Examples section below. Another method of determining at-risk status includes serologic evaluation, for example by anti-VZV antibody ELISA assay. Yet another method is to measure the VZV specific responder cell frequency, RCF, and if found to be about 1 in 68,000, the individual is presumptively at risk. For the purposes of this invention, however, any individual in the population may be considered at-risk as there are no-known side effects of any moment associated with across the board immunization according to this invention, provided that severely immunocompromised individuals, such as those infected with human immunodeficiency virus (HIV) or having full-blown acquired immune deficiency syndrome (AIDS) are not immunized with a live VZV antigen.

The VZV antigen may be a live attenuated VZV, prepared according to the method disclosed in U.S. Pat. No. 3,985,615 (Takahashi) or as disclosed in the examples below. Viability of live attenuated varicella may be maintained in any of a number of known stabilizer formulations. The attenuated Oka VZV is on deposit with the ATCC (aquisition # VR-795) and is also commercially available as VARIVAX®, marketed by Merck & Co., Inc. Other strains of VZV may be used if sufficiently attenuated so as not to cause natural-type disease in naive individuals that may be undergoing vaccination for the first time, or for production of killed or subunit VZV antigens.

The VZV antigen may be an inactvated virus. This material may be prepared simply by as crude a method as heating an aliquot of live VZV and monitoring for the number of residual plaque forming units (PFU) by an appropriate assay or it may be inactivated by more sophisticated techniques such as gamma irradiation, for known amounts of time and intensity. A killed whole-virus is demonstrably as effective in the instant invention as a live VZV, and may be produced by any convenient means, so long as the VZV antigenic integrity is retained. Elevations in anti-VZV responder cell frequencies are the same when heat-killed VZV is used at a dose of about 10 $\mu$g or more or when about 1000 PFU of live virus is administered. Use of a killed whole VZV is preferred, particularly when the recipient is severely immunocompromised.

The antigen may be a VZV subunit antigen or a mixture of antigens which may be purified from VZV or produced by recombinant means. Pure VZV glycoproteins may be produced according to Keller et al., [J. Virol. Methods, 14, 177–188 (1986)]. In one combination, between one and three purified VZV glycoproteins from each of the three classes described in a new nomenclature system [Davison et Al., J. Virol. 57, 1195–1197 (1986)], gpI, gpII, gpIII, is included.

In the method of this invention, whatever the antigen chosen, the following indicia of immunologically effective dose and efficacy of the method are useful:

1. Increase in VZV specific responder cell frequency by about 30% (RCF, see example below).
2. Elevating anti-VZV cytotoxic T-cells (CTL's), as measured by an elevation of VZV specific $CD8^+$ cells (killer cells, see example below).
3. Elevating anti-VZV helper T-cells, as measured by an elevation of VZV specific $CD4^+$ cells (see example below).
4. Increasing the level of anti-VZV specific antibodies.
5. Increasing the level of lymphokines such as interferon, or interleukin.
6. Reducing the duration or severity of post-herpetic neuralgia in an individual to a period of less than one month following development of zoster.

7. Reducing the zoster incidence, on a statistical level, below the incidence found in the general population of similarly at-risk individuals.

There is no generally accepted in vitro method for quantitating cell mediated immune responses in man. We selected limiting dilution cultures with RCF analysis for this study because we anticipated that this approach would be more accurate than measurement of SI. Both methods of analysis showed a significant boost in VZV specific immunity following the immunization. Our preference for the RCF results is based on finding lower standard deviations from mean in these results compared with the SI results. This may in part reflect the fact that 196 tissue culture wells are analyzed to arrive at an RCF estimate, compared with the 6–8 culture wells generally used to calculate SI. Nevertheless, the limiting dilution cultures we used can only give an indirect estimate of the frequency of responders. The denominator used in this study is the number of cells recovered from a Ficoll gradient; of these only one quarter belong to the $CD4^+$ $CD45RO^+$ population, which is the memory phenotype from which VZV-specific responding T cells are drawn [Beverly P C L., *Curr. Top. Microbiol. Immunol.* (1990); 159, 111–112; Hayward A, Giller R, Levin M., *Viral Immunol.* (1989); 2, 175]. Our RCF estimate is therefore likely to underestimate the response to vaccination. Nevertheless, the mean RCF attained after vaccination (1/40,000), is of the same magnitude as that reached after HZ [Hayward A, Kevin M, Wolf W, Angelova G., *J. Infect, Dis.* (1991); 163, 873–875], in which the load of endogenously produced VZV antigen is likely to be large. This level of immunity achieved after vaccination is also comparable to that of asymptomatic individuals 35 to 45 years old. The boost in immune response in the current study was maintained for 24 months with a predicted half-life of 56 months and was not a function of age. This latter property is important since the oldest individuals are most likely to develop HZ and thereby would be the prime targets of a preventive vaccine strategy.

The RCF response after vaccination failed to correlate with dose of vaccine given varying from 1,000–12,000 PFU. Moreover, the frequency of responding subjects is not increased by giving higher vaccine doses. This might represent evidence for replication of the vaccine virus in the recipients, such that even the lowest dose administered eventuates in sufficient VZV antigen for maximal effect on RCF. Alternatively, the relatively large VZV antigen content of the lower doses (e.g. 1,000 PFU contains about 2 units of VZV antigen) may be sufficient for maximal immunization. Only γ-interferon responses of cultured cells correlated with higher dose or younger age.

VZV vaccine effects on VZV antibody were of a lesser magnitude and of shorter duration than effects on CMI. This is probably not critical for the long-term goal of preventing HZ, since titers are known to fall to baseline levels in 1 to 2 years following HZ [Hayward A, Kevin M, Wolf W, Angelova G., *J. Infect. Dis.* (1991); 163, 873–875], and VZV antibody levels do not decline significantly with aging [Miller A E., *Neurology.* (1980); 30, 582–587; Gershon A A, Steinberg S P., *Am. J. Med. Sci.* (1981); 282(1), 12–17]. The mean pre-vaccine VZV antibody levels in our study subjects, as measured by ELISA, was comparable to that of much younger adult controls.

The post-vaccine assessment of immune response included measurement of γ-interferon release by MNC exposed to VZV antigens. This was evaluated as a potentially independent variable because of the in vitro evidence that γ-interferon is made by natural killer cells as well as by antigen-specific T cells [Hayward A R, et al., *Pediatr. Res.* (1986); 20, 398–401]. Natural killer cells and γ-interferon both contribute to the limitation of herpesvirus replication in vitro [Leibson P J, et al., *J. Virol.* (1986); 57, 976–982]. Although a statistically significant increase in in vitro γ-interferon was observed 3 months after immunization, the standard errors were very large. γ-interferon measurement is therefore not a strong predictor of the outcome of VZV immunization.

The following examples are provided to further illustrate the invention, but the invention is not limited to the specifics of these examples.

EXAMPLE 1

Preparation of Live Attenuated VZV Vaccine

A. VZV Production

Live attenuated varicella zoster virus may be prepared according to the disclosure of U.S. Pat. No. 3,985,615, or any of the other methods known in the art.

B. Assay for VZV Yield Determination

The infectivity titers of varicella zoster virus (VZV) preparations were estimated using the agarose-overlay or liquid overlay procedure described by Krah et Al. (*J. Virol. Methods,* 1990, 27:319–326) or by Takahashi et al [*Postgrad Med. J.*] 61 (suppl 4) 736–741, (1985)]. The assay is performed as follows:

MRC-5 cells are seeded in 60-mm tissue culture plates, at $6 \times 10^5$ cells in 5 mL volumes of BME (Basal Medium Eagle with Hanks' balanced salts solution) with 100 mg/L galactose, 50 µg/mL neomycin, 2 mM L-glutamine, and are incubated at 35° C. in a 5% $CO_2$ atmosphere. After incubation for 24–48 hours, the cells reach 50–80% confluency. The growth medium is removed by aspiration, and cells are infected with 100 µl of VZV solution diluted in appropriate virus diluent, such as SPGA buffer, or liquid maintainance medium (LMM). SPGA buffer contains 7.5% (w/v) sucrose, 11 mM potassium phosphate, 0.1% (w/v) sodium glutamate and 1% human serum albumin. Virus is allowed to attach for $\geq 1$ hour at 35° C. in a 5% $CO_2$ atmosphere. The VZV-infected cell cultures are then overlaid with 5 mL agarose overlay medium (AOM) or liquid maintainance medium (LMM). Agarose overlay medium is a mixture of two solutions, liquid overlay medium (LOM) and agarose solution. LOM contains minimal essential medium with Earle's salts (MEM), 2% heat-inactivated fetal calf serum, 50 µg/mL neomycin sulfate and 2 mM L-glutamine. Agarose solution is prepared by heating 4.5 g of low gelling temperature agarose in 100 mL MEM for 15 min at 121° C. and allowing the solution to cool to 45° C. AOM is prepared by mixing one volume of agarose solution with 4 volumes of a 1.25× concentrate of LOM at 45° C. The plates are cooled to 23–25° C. to permit the AOM to solidify. The cultures are incubated to allow plaque development. After 6–7 days, plates which received LOM are overlaid with 5 mL of phosphate-buffered saline (PBS) and rimmed with a glass Pasteur pipette to loosen and remove the agarose. Medium is aspirated from plates which received LMM, and plaques are visualized by staining cells with a solution of 0.2% (w/v) Coomassie Blue R-250 in ethanol-1% acetic acid. Plaque counts are the average of 4–5 replicate plates and expressed as plaque-forming units per mL (PFU/mL).

EXAMPLE 2

Preparation of Inactivated VZV Vaccine

Live VZV, prepared according to the method of Example 1 or by any other method may be inactivated by incubating an aliquot of the virus at about 50° C. for about 5–15 days. Alternatively, live VZV may be inactivated by exposure to gamma irradiation or any other means of inactivating the virus, so long as the antigenic integrity of the virus is not compromised.

In one experiment, live attenuated CR453 VARIVAX® was inactivated as follows:

Heat Inactivation Process: Five hundred vials of lot CR 453 vaccine were heated as unreconstituted, intact vials for 12 days in an incubator at 50° C. Following the heat treatment, all 500 heated vials were marked with prominent, indelible red ink triangles at the center of each vial label and placed at −20° C. storage.

Analysis

Residual infectious varicella virus content in heated vaccine: The determinantion of the number of plaque-forming units was performed as described in Takahashi et al. *Postgrad Med. J.* 61 (Suppl. 4) 736–741 (1985). A total of 5 mL of reconstituted material from 10 vials of heated vaccine was assayed. A value of 2.4 plaque-forming units per mL was obtained. A standard assay of unheated vaccine gave a value of 3830 plaque-forming units per mL.

Varicella virus antigen by dot-blot assay: The determination of viral antigen mass is performed by dot-blot analysis or as described in Example 9 below. The heated product was estimated by dot blot analysis to contain 9.8 units of antigen per mL. The standard unheated vaccine, assayed simultaneously, was estimated to contain 9.4 units of antigen per mL.

Antigen analysis by immunoblots: An experimental Western blot procedure modelled after methods used for other agents was used to compare the antigens in heated and normal vaccines. The two products appeared very similar to each other within the limits of visual observation of immunoblots reacted with either a human polyclonal antiserum or a monoclonal antibody to viral glycoprotein I.

Samples of whole VZV inactivated as described above were used as an immunogen to activate cell mediated immune responses against herpes zoster. Equal doses, equivalent to about 10,000 PFU of live or killed VZV, were administered to people at risk of developing herpes zoster. The antibody response (Ab) and VZV responder cell frequency (RCF) before and 3 months after immunization is summarized below:

| Vaccine | Inactivated | Live |
|---|---|---|
| Number of recipients | 33 | 33 |
| Age of recipients | 67 ± 7 | 64 ± 6 |
| Entry Ab titer | 37.4 (15–91) | 51 (21–123) |
| Ab @ 3 mos. titer | 98.7 (42–227) | 124.5 (58–226) |
| RCF @ entry | 1/63,000 (1/31,000–1/126,000) | 1/71,000 (1/40,000–1/127,000) |
| RCF @ 3 mos. | 1/23,980 (1/8,275–1/69,484) | 1/27,400 (1/11,388–1/66,436) |

These data indicate that substantial enhancement of anti-VZV immune responses are achieved, whether the immunization is with live or killed VZV.

EXAMPLE 3

Preparation of Purified VZV Subunit Antigen

VZV encodes three serologically distinct glycoprotein gene products, GA, GB, and GC [Keller et al., J. Virol. 52, 293–297 (1984)], recently reassigned the names GPIII, GPII and GPI respectively [Davison, et al., *J. Virol* 57, 1195–1197 (1986)]. Substantially homogenous VZV glycoproteins may be prepared as described in Keller et al., [*J. Virol. Methods* 14, 177–188 (1986)]. Briefly, 17 µg of whole VZV was used to immunize balb/c mice in complete Freund adjuvant, followed by a 25 mg intraperitoneal booster without adjuvant, and later an additional 25 µg of VZV was introduced intravenously. Three days later, spleens were removed and spleen cells were fused with SP 2/0 mouse myeloma cells. Hybridoma supernatants were screened for anti-VZV monoclonal antibodies, cloned by limit dilution followed by expansion to produce ascites. The monoclonals were purified and VZV glycoprotein specificity was analyzed by immunoprecipitation.

Monoclonal anitbody affinity resin of defined specificity was produced by coupling 20 µg/gram cyanogen bromide-activated SEPHAROSE 4B (Pharmacia). MRC-5 cells infected with VZV were extracted into 50 mM Tris, pH 7.5, 2% Triton X-100, 4 mM phenylmethylsufonyl fluoride. The cell extracts were dialized against phosphate buffered saline plus 0.05% Triton X-100. Specific glycoproteins were then isolated by binding 20 mL of cell extract with 1 g of monoclonal antibody coupled resin. The slurry was centrifuged, washed and the specific, bound glycoprotein eluted with 3M KSCN. The eluate was diolized against phosphate buffered saline containing 0.05% Triton X-100. In this way purified, gpI, gpII and gpIII glycoproteins were obtained.

Alternate ways of generating substantially homogenous VZV glycoproteins include recombinant production of specific VZV gene products. Thus, the methods of Ellis et al., [*J. Virol.* 53, 81–88 (1985)], or Keller et al., [*Virology* 152, 181–191 (1986)] may be used.

EXAMPLE 4

Anti-VZV Skin Test

A varicella skin test is performed by subcutaneaus introduction of a VZV antigen or control antigen, followed by measurement of erythematous changes about 48 hours often the introduction of antigen. Accordingly, the method of Kamiga et al., [*J. Inf. Dis.* 136, 784–788 (1977)] Babu et al., [*J. Clin. Microbiol.* 25, 2193–496, (1987)] or Lafussa et al., [*J., Inf. Dis.* 152, 869–875 (1985)] may be used to perform the skin test. Alternatively, the inactived antigen, prepared as described in Example 2, or the purified antigen of Example 3, could be used to provide the VZV antigen. In any event, a negative skin test antigen assay was shown by Takahashi [*Adv. Virus. Res.* 28, 285–356 (1987)] to closely correlate with susceptibility to variella infection. In this regard, VZV plycoproteins with molecular weights of 15,000 and 45,000 which are closely associated with cell-mediated immunity, are preferred as indicators of susceptibility to zoser reactivation.

EXAMPLE 5

Assay for VZV Responder Cell Frequency

VZV responder cell fequencies may be measured according to methods known in the art for example, limiting dilution analyst is described by M. Zauderer [Handbook of Experimental Immunology, Volume 2—Cellular Immunology, Blackwell Scientific Publications, D. M. Weir, et al.,—editors, (1986)—Chapter 65]. Also, see the disclosure in Example 7 below, section 5: "Determination of the frequency of blood mononuclear cells (MNc) which proliferate in response to VZV antigen."

According to the method of this invention, levels of responder cells approaching about one responder cell in 40,000 are achieved which is the same level of RCF found in post-zoster individuals.

EXAMPLE 6

Assay for Anti-VZV Cytotoxic T-Cell Level

VZV cytotoxicity assay: Peripheral blood monocytes (PBMN) are separated and cultured with live VZV, in microwells at $10^4$ cells/well. After 7 days, 1 unit of IL2 is added to each well and culture continued for 10 days, when the plates are examined by eye to detect wells with growth. Blast cells are recovered from these wells and restimulated with the homologous antigen and autologous EBV cells (5000 r irradiated) and 10 u/ml IL2 for a week of clonal expansion. Use of live VZV to stimulate in this context derives from Braciale and co-workers' evidence [*Immunol. Rev.*, 98, 95 (1987)] that a live virus stimulus is required to elicit class I restricted responses, and from data [Arbeit et al., *Intervirology* 18, 56 (1982)] that monocytes are infectable by VZV, and the need for autologous cells bearing both class I and II for antigen presentation.

The cells from responder wells are tested for MHC restriction primarily by inhibition of cytotoxicity [Gaston et al., *Immunogenetics* 19, 475–486 (1984)]. T cells are suspended to $10^6$/ml, and $10^5$ cells are added to $5 \times 10^3$ autologous or unrelated targets preincubated with VZV. MHC restriction is determined (1) by phenotyping an aliquot of the effector cells for CD4 and CD8 and (2) adding 1 $\mu$g/ml of W6/32 (ATCC Hybridoma Bank HB 95, anti-class I) or HB55 (ATCC, anti-class II) to the cytotoxicity assays. These antibodies are suitable because they suppress the deveopment of class I and class II restricted cytotoxic cells respectively in mixed lymphocyte culture. $^{51}$Cr release from the target cells is measured after 6 hours incubation.

Class I MHC restricted cytotoxic cells are identified as inhibitable by W6/32 and CD8 phenotype. Class II restricted cytotoxic cells are inhibited by HB55 and the effectors are CD4. Results from PBMN obtained at different intervals after acute VZV in young adults, and before and after the OKA booster immunization are compared.

EXAMPLE 7

Immunizing Adults At-Risk of Developing Herpes Zoster

1. Population

Individuals 55 to 87 years old were vaccinated if they had a history of prior varicella, but had never had HZ. Excluded were those with a debilitating or immunosuppressive illness and those receiving immunosuppressuve therapy. We also excluded anyone who received another vaccine within a month before or anticipated receiving another vaccine in the month after VZV vaccination, and individuals who received gamma globulin therapy within three months before VZV vaccination.

2. Vaccine

Live attenuated vaccine (Oka/Merck Strain) was stored at −20° C. in a lyophilized state and reconstituted with distilled water to an infectivity titer of 1,140 pfu/0.5 ml (lot CR 452) or 3,010 pfu/0.5 ml (lot CR 320). Other live Attenuated varicella zoster viruses may also be employed. The preferred Oka virus may be prepared according to the disclosure of U.S. Pat. No. 3,985,615, herein incorporated by reference for that purpose.

3. Design

Potential vaccinees were stratifield by age (55–59; 60–64; 65–69; 70–79; $\geq$80 years old). Individuals in each age cohort were randomly assigned to receive one of four doses of vaccine subcutaneously: 3,010 pfu; 6,020 pfu; 12,040 pfu; or 3,010 pfu with a booster dose of 3,010 pfu 3 months after the first dose. Additional individuals 55–59 years old were randomly chosen to receive 1,140 pfu.

Blood was obtained from vaccinees for immunological assessment just prior to imunization and at 3, 12 and 24 months post immunization. Blood was also obtained three months after the booster dose.

Vaccinees were followed for vaccine reactions for 42 days with biweekly telephone calls. Vaccinees also recorded signs and symptoms on a vaccination report card. They measured their temperature daily for 5 days after vaccination, and thereafter only if they felt febrile. Those with unusual reactions were assessed individually. Skin lesions were cultured for VZV. Patients were instructed to call whenever they thought they had developed HZ. In addition, during the first year they were called monthly to inquire about HZ, and they were similarly questioned at the end of the second year. Skin lesions or pair syndromes thought to represent HZ were investigated by physical examination, culture of lesions for VZV, and acute and convalescent (4–6 weeks after suspect HZ) VZV-specific immunologic assessment.

4. Detection of IgG Antibody to VZV Antigen by Enzyme-Linked Immunosorbent Assay (ELISA)

Rows A to D of IMMULON 11 plates (Dynatech, Alexandria, Va.; Cat. No. 011-010-3450) were coated with 0.1 ml of VZV antigen and rows E to H with control antigen (M.A. Bioproducts, Walkerville, Md.; Cat. No. 30-149J for VZV antigen; 30-150J for control) diluted 1:20 in phosphate-buffered saline (PBS; 0.15 M, pH 7) overnight at 4° C. The plates were rinsed in PBS and blocked with 1 mg/ml gelatin in PBS overnight. Patient and control positive sera were added to antigen and control wells in four-fold dilutions (starting at 1:50) and incubated overnight at 4° C. Subsequent incubations were with peroxidase-conjugated affinity-purified goat anti-human IgG (Tago, Burlingame, Calif.; Cat. No. 2390), diluted 1:2000 in PBS, and with ABTS substrate (Sigma, St. Louis, Mo.). Color was developed for 30–60 min, and the OD read on a DYNATECH plate reader with ELISACALC software. Optical densities of the control wells were substracted from the VZV wells. An aliquot of a single positive reference serum was run in all plates and a regression line for log (dilution) against log (OD) calculated. The VZV antibody in subject samples was expressed as percent of the reference serum.

5. Determination of the Frequency of Blood Mononuclear Cells (MNC) which Proliferate in Response to VZV Antigen MNC were separated from heparinized blood by Ficoll-Hypaque centrifugation, washed in Hanks balanced salt solution, and cultured in RPMI 1640 medium supplemented with antibodies and 10% autologus serum. Details of the limiting-dilution cultures used to determine the responder-cell frequency (RCF) are published [Feldman S, et al., *Am. J. Dis. Child.* 126, 178–184 (1973)]. Briefly, 24 replicate cultures containing 100,000, 50,000, 25,000, and 12,500 MNC per well were cultured with a 1:200 dilution of cell-free VZV antigen for 10 days and then pulsed for 8 hr with 0.25 $\mu$Ci[$^3$H]thymidine (TRK 61, Radiochemical Centre, Amersham; 5 Ci/mmol) per well. Parallel control cultures were identical except that they were stimulated with a diluted control antigen prepared from uninfected cells. Responder wells were defined as those with greater than the mean plus 3 SD cpm of the 24 replicate parallel control cultures. RCF was interpolated, in a plot of the log of the percent non-responder wells against the cell number per well, as the point at which 37% of VZV antigen-stimulated wells were nonresponders [Henry C, et al., In Mishell B B, Shiigi S M eds. *Selected Methods in Cellular Immunology.* San Francisco: Freeman Press, (1980)]. RCF if expressed as the mean number of MNC required to detect one VZV-specific proliferating cell.

In 2% of subjects the mean cpm in the unstimulated wells containig $10^5$ cells artifactually increased the percentage of non-responder wells. We, therefore, calcualted the RCF in this subset of subjects from the data points at 12,5000; 25,000; and 50,000 cells per well. The great reliance placed on data points at lower cell numbers in these subjects is justified by the greater linearity of the data points.

To obtin a stimulation index from these cultures, the arithmetic mean for the stimulated and unstimulated wells was determined, and expressed as (stimulated cpm/unstimulated cpm).

6 γ-Interferon Production in VZV-Stimulated MNC Cultures

Cultures of $5\times10^5$ MNC in 0.5 ml were incubated with a 1:20 dilution of control or VZV antigen. After 5 days supernatants were assayed for γ-interferon by ELISA (Amgen, ABC 3,000; Thousand Oaks, Calif.). The results are expressed as international units (IU)/ml.

7. VZV Isolation

Isolation of VZV from skin lesions was attempted by culture in human embryonic lung fibroblasts (derived locally; passage 10 to 20) after scrapping papules or vesicles and vigorously swabbing the base. VZV was identified by specific immunofluoscience.

8. Statistics

Simple comparisons were made with Student's t tests at the 0.05 significance level with Bonferroni adjustment where appropriate. The effects of gender, age, vaccine dose, and number of months post-immunization were assessed via repeated measures analysis [Laird N M, Ware J H., *Diometrics* (1982); 38, 963–974; Jennrich R, Schluchter M D., *Biometrics* (1986); 42, 805–820]. In order to investigate the duration of immunity, inverse polynomial models were fit using a non-linear analogue of the Laird and Ware model [Nelder J A., *Biometrics* (1966): 22, 128–141; Hirst K, et al., *Commun. Stat.* (1991): B20].

RESULTS

A total of 202 individuals were immunized. The mean age of the 138 female vaccinees was 65.8±7.3; the mean age of the 64 male vaccinees was 67.7±6.5 years. Eight to 15 subjects in all dose categories were ≧80 years of age.

The vaccine was generally well tolerated. Fewer than 25% of vaccinees had local reactions

TABLE 1

Local reactions to the varicella vaccine in elderly immune individuals

| Type | First Injection[1] (%) | Booster Injection[2] (%) |
|---|---|---|
| Erythema | 47 (23) | 3 (7) |
| Swelling | 30 (15) | 2 (5) |
| Tenderness | 22 (11) | 0 |

TABLE 1-continued

Local reactions to the varicella vaccine in elderly immune individuals

| Type | First Injection[1] (%) | Booster Injection[2] (%) |
|---|---|---|
| Erythema/Swelling | 29 (14) | 0 |
| Erythema/Swelling/Tenderness | 13 (6) | 0 |

[1]n = 202
[2]n = 43

These consisted of erythema, swelling, and/or tenderness. Mean duration of local reactions were 2.9 days for erythema, 2.9 days for swelling, and 3.6 days for tenderness. These reactions were neither more frequent nor more severe in vaccinees receiving booster doses. Temperature greater than 100° F. occurred in <1% of vaccinees.

TABLE 2

Complaints in the 6 weeks following varicella vaccine in elderly immune individuals

| Frequency | Type |
|---|---|
| 4% | Headache |
| <3% | Sore eyes, stiff neck, myalgia rash |
| <2% | Arthalgia, abdominal pain |
| <1% | Sore Throat, earache, swollen glands, nausea, cough, diarrhea, fever (>100° F.). |

A variety of other, mild symptoms occurred in ≦4% of vaccinees.

Eleven patients complained of a rash within 40 days of vaccination.

TABLE 3

Rash after varicella vaccine for elderly immune individuals
Early Rash (<40 days)

| | | VZV | |
| Type | Patients[1] | Day Onset | Isolated |
|---|---|---|---|
| Papules (1–10)[2] | 4 | 3,7,8,14 | 0/4 |
| Macules (4;?) | 2 | 5,15 | 1/1 |
| Marked Erythema/Induration at Injection Site | 2 | 3,3 | ND[3] |
| Other (bruise, contact, dermatitis, dry skin) | 3 | — | ND |

[1]Total injections = 245
[2]Numbers in parentheses indicate the range of number of lesions; unknown for one vaccinee.
[3]ND = not done Two of these individuals proved to have only local erythematous reactions to the vaccine. Six individuals had maculopapular rashes comprising 1 to 10 lesions which appeared 3 to 15 days after immunization. VZV was isolated from only one of the five patients whose lesions were tested. This VZV proved to be wild-type by restriction enzyme analysis.

Antibody levels in elderly subjects were at 85% of a control standard reference serum prior to immunization. After varicella vaccine was administered, antibody levels were significantly higher for 12 months (p<0.001), but not at 24 months post-vaccination (p=0.100). Dose, gender, and age did not affect this response. In vitro production of γ-interferon by VZV stimulated T cells was also significantly higher (p<0.001) at 3 and 6 months after immunization (FIG. 2), but this effect was lost by 12 months. Higher vaccine doses (p=0.037) and younger age (p.-0.023) were associated with higher γ-interferon responses.

Cell Mediated Immunity

To measure cell mediated immunity to VZV antigen following booster immunization, the subjects' MNC were cultured using different numbers of cells per well. These cultures were analyzed as limiting dilution cultures to obtain an approximation to the frequency of VZV-specific T cells in the blood (RCF). We used this approach because we anticipated that it would be easier to quantitate and compare data points over several years of study. Prior to receiving the vaccine the subjects had a mean RCF of 1:68,000 (i.e. one VZV-specific proliferating cell per 68,000 peripheral blood MNC). This increased to 1:40,000 by six months after vaccination, and remained significantly above pre-immunization levels for 24 months (FIG. 3)(p=<0.001). The magnitude of the mean improvement in RCF is probably an underestimate, since 33% of vaccinees who had less than one responder cell in 100,000 MNC prior to vaccination are included in our analysis as having one responder cell. The absolute value of RCF at 12 or 24 months after vaccination Post vaccine immunity was lost at the rate of 309±364 cells/responder cell/month (95% confidence limits=0–1,047 cells). RCF correlated poorly with antibody or γ-interferon responses.

It was noted that a cohort of vaccinees failed at any time after vaccination to have more that 1 RCF/$10^5$ MNC. This non-responder cohort was similar (8 to 20%) in all age groups, except for vaccinees more that 80 years of age, among whom 5 of 8 were non-responders. There was no statistically significant correlation between age and non-response, nor did non-response correlate with the dose of vaccine administered.

The enhancement of VZV immunity was also detected when the data were expressed as a stimulation index. These results were log transformed for analysis because they were logarithmically distributed. At entry, the mean stimulation index was 3.44 (1 SD range 1.2–9.9); at 3 months was 4.57 (1.6–12.8); at 1 year was 4.85 (1.81–13.5) and at 2 years was 4.58 (1.7–17.1).

Protection From HZ

Seven patients were evaluated for possible herpes zoster (Table 4) over two years (corresponding to 400 patient-years of observation). The results of this analysis are shown in Table 4 below:

TABLE 4

RASH and/or PAIN AFTER VARICELLA VACCINE FOR ELDERLY IMMUNE INDIVIDUALS

| Type | Age | Onset 1 (Months) | VZV Isolated | RCF (Acute/ Convalescnet) | Cause[2] | Pain Duration) |
|---|---|---|---|---|---|---|
| Thoacic Dermatome Ulcers | 78 | 1.3 | 0 | ND[3]/1:19,000 | Local tramua | 0 |
| Unilateral Hard Palate Ulcers/Local Dysesthesia | 69 | 3.5 | 0 | 1:100,000/ 1:17,000 | Probable HZ | 0 |
| Dermatomal Vesiculo- pustular left scalp | 70 | 17 | + | 1:26,000/ 1:30,000 | HZ | mild (4 day) |
| Pain Right ear; lancinating Q 5–10 min; ± relief with asprin | 78 | 7 | no lesions | 1:100,000/ 1:40,000 | Possible HZ | mild (4 day) |
| Buttock Vesicles | 81 | 2 | HSV II Isolated | ND[3] | HSV II Reactivation | 0 |
| Disseminated Vesicles (2 patients); Non-dermatomal | 64/65 | 10 | ND | ND | Cat mites | 0 |

[1]Months after initial immunization
[2]Cause assigned based on clinical, virological, and immunological date.
[3]ND = not done.

was not a funciton of gender, dose administered, or age of the vaccinee. However, the incremental improvement in RCF (i.e. the RCF at 12 or 24 months less the RCF prior to vaccination) was greater in older individuals (p<0.05), reflecting the relatively poor CMI (i.e. lower RCF) in older individuals before immunization and the fact that all responding vaccinnes—regardless of age—achieved similar post-vaccine levels. Inverse polynomial modeling of the data predicted that maximal RCF was achieved at 6.34 months, with half of this effect remainig for 55.9 months.

One yielded VZV in culture from skin lesions. Three others had compatible clinical presentations, two of whom had improvement in covalecent RCF suggestive of recent VZV infection. One patient had complete immunologic assessment, and three others had no immunologic assessment because their lesions were not due to VZV. Only two suspect cases had acute pain (4 days duration each) and none had pain after the lesions healed (post-herpetic neuralgia).

EXAMPLE 8

Preparation of a VZV Subunit Vaccine

The subunit antigen of Example 3 is formulated with aluminum hydroxide gel and administered at a dose of about 0.1 micrograms/kg–1 milligram/killogram.

EXAMPLE 9

Competititve ELISA for Quantitation of VZV Antigen

Because the VZV plaque assay is time consuming, it is not particularly amenable to in-process control. A rapid VZV antigen ELISA permits measurement of VZV antigen amounts to permit monitoring of virus growth during manufacture of live varicella vaccine. Additionally, this test can be used to estimate VZV antigen amounts in clarified, sonicated vaccine bulks, and potentially to measure antigen in filled lyophilized vaccine vials. Briefly, this assay is conducted by incubation of VZV antigen from test samples with anti-VZV serum in solution. Remaining free antibody is allowed to bind to VZV antigen immobilized on ELISA microtiter plates. The amount of antibody capable of binding to the plates is inversely proportional to the amount of antigen in the test sample. Antibody binding to the plates is quantitated by reaction with an enzyme-linked anti-human antibody and appropriate substrate to provide a colored product which is quantitated spectrophotometrically.

The VZV antigen ELISA and the VZV plaque assays should generally provide correlative data, but it should be borne in mind that the VZV antigen assay detects non-viable as well as viable VZV. The antigen assay is also valuable in that it provides a measure of the total antigen load being administered to a VZV vaccine recipient.

Test Procedure

1. ELISA plates are coated with glycoproteins (gps) from VZV-infected or uninfected MRC-5 cells, and are over-coated with 1% bovine serum albumin [fraction V, #A-9647, Sigma], 0.1% $NaN_3$) to reduce non-specific adsorption of antibodies to the plates. Alternating rows are coated with VZV or control antigen (i.e. rows A, C, E, and G receive VZV gp and rows B, D, F, and H receive uninfected MRC-5 gp antigen).
2. Clarified (3250 g-min) test antigen is diluted in stabilizer in 12×75 mm tubes or microtubes. A standard virus antigen preparation (26 units/mL VZV antigen by dot blot assay) is diluted 1:10 and then serially 1:1.25-fold to provide antigen concentrations of 2.6, 2.1, 1.7, 1.3, 1.1, 0.9 units/mL. Additional dilutions may be included to provide 0.7 and 0.5 units/mL of antigen. This dilution series is used to generate a standard curve for the measurement of antigen amounts in test samples.

3. A human anti-VZV serum is diluted in stabilizer to 2 times the final desired dilution.
4. Three hundred $\mu$l volumes of diluted antigen are dispensed into microtubes, mixed with 300 $\mu$l diluted anti-VZV serum and incubated at 35° C. for 15–22 min. A control includes human anti-VZV and diluent (no antigen).
5. Aliquots of 100 $\mu$l from each serum-antigen mixture are added to 2 replicate VZV glycoprotein (VZV gp) coated wells and 2 MRC-5 gp coated wells (4 wells per sample) (e.g.: sample 1 in column 1, rows A, B, C, and D; sample 2 in column 2, rows A, B, C, and D; etc.).
6. Plates are incubated for 15±1 minute at 35° C. to allow free antibody (not complexed to antigen in solution) to bind to virus antigen immobilized on the plates.
7. Unbound antibody is removed by washing and wells receive an alkaline phosphatase conjugated goat anti-human IgG to detect bound human antibody.
8. After incubation for 15±1 minute at 35° C., unbound conjugate is removed by washing. Bound conjugate is detected by incubation for 15 min at 35° C. with p-nitrophenyl phosphate substrate dissolved in diethanolamine buffer.
9. After termination of the substrate reaction by addition of 50 $\mu$l/well 3 M NaOH, color development (OD at 405 nm) is quantitated using a microplate spectrophotometer.

Test Calculations and Interpretation

1. Respective replicate OD values for the replicate VZV and MRC-5 coated wells are averaged. Experience has shown the MRC-5 OD to be consistent between different samples and dilutions. Therefore, the MRC-5 values for the entire plate are averaged and used to correct for non-specific binding of the primary antibody or conjugate to uninfected cell extracts. The averaged MRC-5 OD is subtracted from the respective averaged VZV ODs to provide VZV-specific OD (ΔOD) values.
2. Generation of a standard curve for measurement of antigen amounts:
   The standard curve ΔOD values are plotted against the known antigen concentrations (units VZV/mL). The data are entered into an appropriate graphics program (e.g.: Cricket Graph version 1.3, Cricket Software, Malvern, Pa.), the linear portion of the curve is identified (must include at least 4 points), and the "line fit formula" (y=a+bx) is obtained.
3. Calculation of antigen amounts of test samples:
   Values for a and b are given by the line-fit formula, and y (ΔOD) is known. The remaining unknown value, x, representing the units/mL antigen, can then be calculated, and corrected by the sample dilution to obtain the antigen concentration of the undiluted sample. A sample general calculation follows:

| Sample | Dilution | ΔOD | units/mL antigen from line formula | units/mL antigen corr for dilution |
|---|---|---|---|---|
| A | 1:2 | Y | X = (y − a)/b | (x)*(dil factor) |

The reported antigen concentration is that obtained with the least diluted sample providing a ΔOD value within the linear portion of the standard curve.

EXAMPLE 10

Clinical Studies

The method for testing the efficacy of an anti-zoster vaccine is as follows:

a. A pre-vaccination value of VZV responder cell frequency, anti-VZV antibody and VZV specific cytotoxic T-cell levels from a population of zoster susceptible adults is obtained;
b. A first sufficiently large population of VZV susceptible adults is vaccinated with a live, inactivated or subunit VZV vaccine and a second sufficiently large population (control) of similar adults is vaccinated with the VZV vaccine diluent minus live, inactivated or subunit VZV;
c. A post-vaccination value for responder cell frequency, anti-VZV antibody and VZV specific cytotoxic T-cells is obtained;

d. The values obtained in (c) are compared with the values obtained in (a) such that about a 30% increase in VZV responder cell frequency, an increase in VZV specific antibodies and an increase in VZV specific T-cells within 3 months post-vaccination is indicative of anti-VZV vaccine efficacy.

What is claimed is:

1. A method of immunization which comprises immunizing a person older than fifty who has had varicella or who has had a live varicella vaccine with an immunologically effective amount of attenuated varicella zoster virus Oka strain, where said amount is at least 1,000 plaque forming units (PFU), thereby reducing the severity of post-herpetic neuralgia.

2. The method of claim 1 where said immunizing is done subcutaneously.

3. The method of claim 1 where the attenuated varicella zoster virus Oka strain is stored in a lyophilized state.

4. The method of claim 3 where the attenuated varicella zoster virus Oka strain is reconstituted with distilled water.

* * * * *

UNITED STATES PATENT AND TRADEMARK OFFICE
CERTIFICATE OF CORRECTION

| | | |
|---|---|---|
| PATENT NO. | : 6,214,354 B1 | Page 1 of 1 |
| APPLICATION NO. | : 09/372535 | |
| DATED | : April 10, 2001 | |
| INVENTOR(S) | : Gary B. Calandra et al. | |

It is certified that error appears in the above-identified patent and that said Letters Patent is hereby corrected as shown below:

On the title page, item [73] following the heading ASSIGNEE:

Delete "Merck & Co., Inc., Rahway, NJ (US)" and insert

-- Merck & Co., Inc., Rahway, NJ (US) and The Regents of the University of Colorado, Boulder, CO (US) --

Signed and Sealed this

Ninth Day of June, 2009

JOHN DOLL
*Acting Director of the United States Patent and Trademark Office*